United States Patent [19]
Barton et al.

[11] 3,953,424
[45] Apr. 27, 1976

[54] AZETITIN-2-ORES AND PROCESS FOR PREPARING SAME

[75] Inventors: Derek Harold Richard Barton; Peter George Sammes, both of London, England

[73] Assignee: Glaxo Laboratories Limited, Greenford, England

[22] Filed: Sept. 12, 1972

[21] Appl. No.: 288,353

[30] Foreign Application Priority Data
Sept. 21, 1971 United Kingdom............... 44034/71

[52] U.S. Cl.......................... 260/239 A; 260/239.1; 260/243 C; 260/949
[51] Int. Cl.²...................................... C07D 205/08
[58] Field of Search............................... 260/239 A

[56] References Cited
UNITED STATES PATENTS
3,755,342   8/1973   Heusler et al................... 260/239 A FOREIGN PATENTS OR APPLICATIONS
2,138,320   5/1972   Germany......................... 260/239 A Primary Examiner—Henry R. Jiles
Assistant Examiner—Robert T. Bond
Attorney, Agent, or Firm—Bacon & Thomas

[57] ABSTRACT

Novel azetidin-2-ones having in the 4-position an S-attached saturated or unsaturated, substituted or unsubstituted aliphatic group having at least 2 carbon atoms and in the 3-position an amino or blocked amino group are provided. The novel compounds are useful as intermediates in the production of cephalosporins, penicillins and related β-lactam antibiotic compounds. The novel compounds are prepared by cleaving a penicillin-1-oxide in the presence of a compound containing a nucleophilic carbon-carbon multiple bond not forming part of a ring.

6 Claims, No Drawings

AZETITIN-2-ORES AND PROCESS FOR PREPARING SAME

This invention relates to a process for the production of novel semisynthetic intermediates or relay compounds of use in the production of cephalosporins, penicillins and related β-lactam antibiotic compounds.

The first total synthesis of a cephalosporin antibiotic was achieved by R. B. Woodward (J.A.C.S. 1966, 88, (4), 852) starting from L(+)-cysteine and proceeding via about eight synthetic steps to a β-lactam (i) which was then converted into a cephem (iii) by the following reaction sequence.

ical configuration requires extremely careful control of the stereochemistry at several points. We have now found that intermediates closely similar to Woodward's compound (i) can be produced from penicillins; this conversion proceeds more readily and in fewer stages than the production of (i) from L-(+)-cysteine and has the merit of starting from a β-lactam of the required steric configuration. Furthermore, penicillins, particularly penicillins G and V, are generally cheaper to produce, e.g. by fermentation, than L(+)-cysteine.

In our Belgian Patents Nos. 770726, 770727, 770728, 770729, 770730 and 770731, we have described the production from penicillins of compounds which can be represented by the formula:

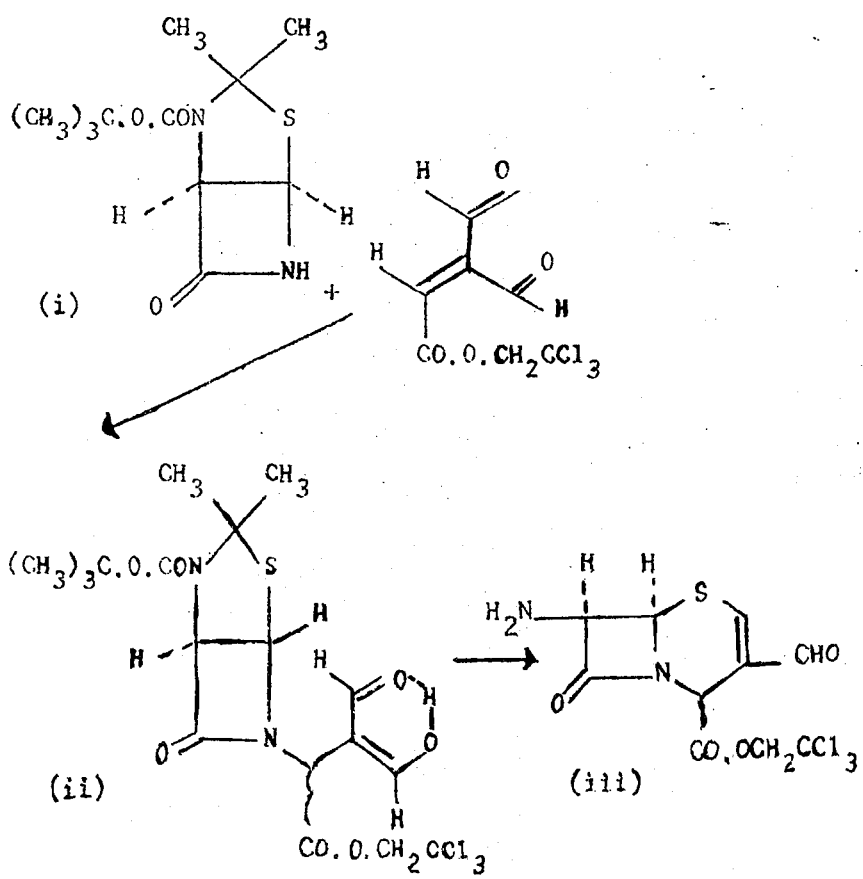

The compound (i) thus constitutes a valuable intermediate in the preparation of cephalosporins and other β-lactam antibiotics; by reaction with an analogous aldehyde reagent it is also possible to convert (i) into a penicillin and it will be appreciated that in this way penicillins having varying substitution in the 5-membered ring can be produced. Similarly by replacing the 2,2,2-trichloroethyl 3,3-diformylacrylate reagent by suitably substituted alternatives, a series of cephalosporin analogues can be prepared.

R. B. Woodward started from L(+)-cysteine in order to achieve a total synthesis. However, this material is relatively expensive and even more significantly, its conversion into a β-lactam of the required stereochem-

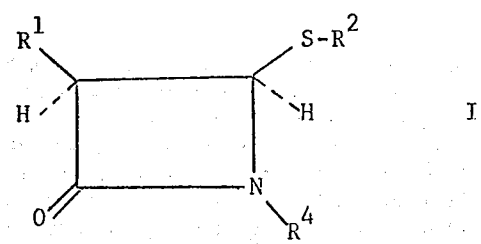

where $R^1$ is an amino group or a blocked amino group, including in particular groups NH.COR which are sidechains present in the 6-position in penicillins; $R^2$ is an acyl group (including a sulphonyl, sulphinyl or phosphoryl group), an aliphatic, araliphatic or aromatic group or a group —S—R³, where R³ is either the residue of a thiophilic sulphur nucleophile or a group of the formula

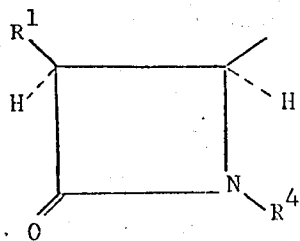

or R¹ and R² together with the sulphur atom form a group

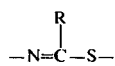

where R is the residue of an acyl group RCO— and R⁴ is a hydrogen atom or an aliphatic, aromatic, araliphatic or acyl group.

The compounds of formula I possess the β-lactam ring structure of the penicillins from which they were derived, with the same steric configuration. They are thus very suitable intermediates for the production of further penams and the related cephams which have this β-lactam structure in common whereas the synthesis of Woodward required very careful control to achieve a suitable β-lactam configuration as is stated above.

The compounds of formula I in which R¹ and R² together with the sulphur atom form a group

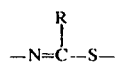

are obtained by internal "trapping" of the penicillin sulphur atom by the carbonyl group of the 6-acylamino group during cleavage. Compounds in which R¹ and R² constitute separate groups result from external trapping of the sulphur atom during cleavage.

The present invention is concerned with the preparation of related intermediates by external trapping, this being effected by nucleophilic substitution on the sulphur atom by a compound containing a multiple carbon-carbon bond.

Thus, it is possible to prepare useful azetidin-2-ones having in the 4-position an S-attached saturated or unsaturated, substituted or unsubstituted aliphatic group having at least 2 carbon atoms and in the 3-position an amino or blocked amino group, by cleavage of a penicillin 1-oxide of formula II

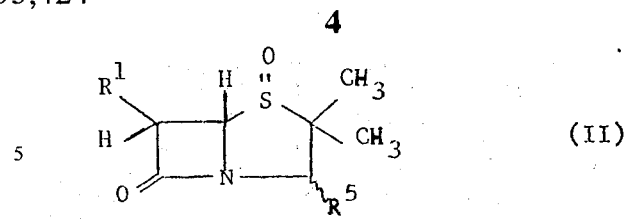

where R¹ is an amino group or a blocked amino group and R⁵ is a hydrogen atom, a hydroxyl or amino group, a protected hydroxyl or amino group, a carboxyl or blocked carboxyl group or an aliphatic, aromatic, araliphatic or acyl group, in the presence of a compound containing a nucleophilic carbon-carbon multiple bond not forming part of a ring. Such compounds typically include compounds of formula III

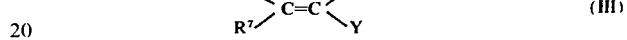

where X is an electron-donating group; Y is a group as defined for X, a hydrogen atom or an aliphatic, cycloaliphatic, araliphatic or aryl hydrocarbyl group, or X and Y together with the carbon atom to which they are attached form a heterocyclic ring; and R⁶ and R⁷, which may be the same or different, are each a hydrogen atom or an aliphatic, cycloaliphatic, aromatic or araliphatic group or a group as defined for X, or R⁷ and Y constitute a carbon-carbon bond.

In view of the inherent nucleophilic properties of carbon-carbon multiple bonds it is also possible to cleave penicillin 1-oxides of formula II in the presence of compounds of formula III in which X is a radical not having electron-donating properties. Thus, for example, compounds of formula III in which X represents a hydrogen atom or an aliphatic, cycloaliphatic, araliphatic or aryl hydrocarbyl group or in which X and Y together form a carbocyclic ring may be used to effect trapping of the penicillin sulphur atom.

In general the initial product of the reaction can be represented as a transient intermediate of formula IV

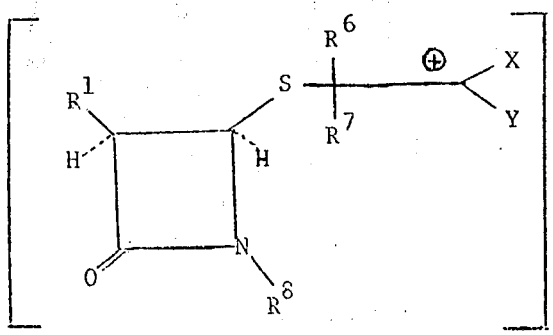

where R¹, R⁶, R⁷, X and Y are as defined above, and R⁸ is a hydrogen atom or a group

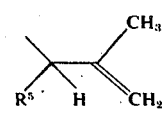

or

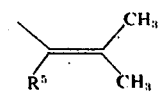

where $R^5$ is as defined above, except that if $R^5$ in the starting material is a free amino or hydroxyl group, the group $R^8$ in the carbonium ion of the compound of formula IV will spontaneously eliminate to yield a compound in which $R^8$ is a hydrogen atom.

When $R^5$ in formula II is other than a free hydroxyl or amino group, being, for example, an acylamino group such as a urethane, an esterified hydroxyl group, a carboxyl group or an esterified carboxyl group, then the group $R^8$ in the initial product of formula IV will normally have the formula

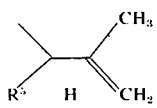

Where $R^5$ is a carboxyl or esterified carboxyl group, such an isopropylidene group can, if desired, be readily converted to an isoprenyl group of formula

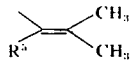

by, for example, treatment with a base, or may be formed spontaneously.

When the group $R^6$ in formula IV is a hydrogen atom, the compound of formula IV may react further by elimination of a proton, to yield a compound of formula V

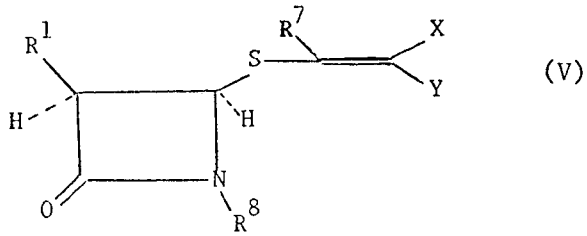

the symbols being as defined above.

It will be appreciated that the unsaturated reagent III and the product of formula V may exist in cis or trans forms, or as mixtures of these.

Alternatively, when $R^6$ and $R^7$ comprise hydrogen atoms or organic groups, i.e. $R^7$ and Y do not together constitute a carbon-carbon bond, and particularly when the groups X and/or Y tend to stabilize the carbonium ion of the compound of formula IV, the ion may react with a hydroxide ion deriving from the penicillin cleavage, to yield a compound of formula VI

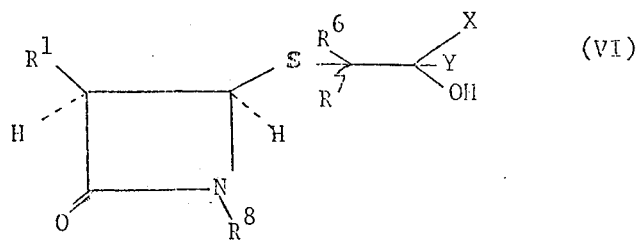

which compound will often undergo (particularly when Y is a further electron-donating group such as an ether group) subsequent rearrangement and elimination of a species HX to yield a carbonyl derivative of formula VII

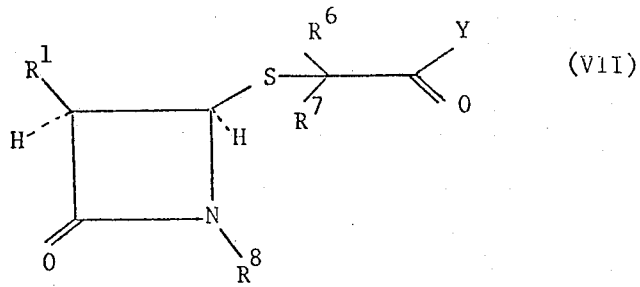

the symbols in each formula being as defined above.

Compounds of formula VII in which $R^8$ is a hydrogen atom may undergo further rearrangement, particularly if Y is also a hydrogen atom, with attack of the side chain carbonyl group at the β-lactam nitrogen atom resulting in formation of a cyclic carbinolamine.

Where such a reactive carbonyl group will be formed the group $R^1$ in compounds of formula VII preferably does not contain replaceable hydrogen atoms; otherwise reaction may occur between $R^1$ and the S-attached side chain. Thus it is undesirable that there should be any —NH— groupings in the group $R^1$.

In the above formulae $R^1$ is a blocked amino group. As used herein, the term 'blocked' means that the group concerned carries at least one substituent and is no longer a free amino, carboxyl or hydroxyl group. The term 'protected' as used herein means that the group concerned carries at least one substituent which can be removed selectively without undue damage to the rest of the molecule, e.g. by hydrolysis, hydrogenolysis or reduction.

$R^1$ may thus be a protected amino group and this may be conveniently one of the groups set out in the following table.

| Type | Example | Usual Name and Analogues etc. |
|---|---|---|
| Urethane | HNCOCH₂Ph ‖ O | Benzyloxycarbonyl p-Methoxy |
| Urethane | HNCOC(CH₃)₃ ‖ O | t-Butoxycarbonyl |
| Urethane | HNCOCHPh₂ ‖ O | Diphenylmethoxy-carbonyl |
| Urethane | HNCO—(1-adamantyl) ‖ O | 1-Adamantyloxy-carbonyl |
| Arylmethylamino Onium | HNCPh₃ NH₃⁺ | Trityl |
| Urethane | HN·CO·OCH₂CCl₃ | β,β,β-trichloro-ethoxycarbonyl |

R¹ can also be a group NHCOR, wherein R can be defined generally as hydrogen or an organic group which preferably contains 1–20 carbon atoms. Such groups are usually present in the penicillin and cephalosporin antibiotics.

In general, the following main classes are especially suitable for the acyl group RCO—:

i. $R^u C_nH_{2n}$—CO where $R^u$ is aryl (carbocyclic or heterocyclic), cycloalkyl, substituted aryl, substituted cycloalkyl, optionally substituted cyclohexenyl, optionally substituted cyclohexadienyl, or a nonaromatic or mesoionic heterocyclic group, and n is an integer from 1–4. Examples of this group include phenylacetyl; substituted phenylacetyl e.g. fluorophenylacetyl, nitrophenylacetyl, aminophenylacetyl, acetoxyphenylacetyl, methoxyphenylacetyl, methylphenylacetyl, or hydroxyphenylacetyl; N,N-bis (2-chloroethyl) aminophenylpropionyl; thienyl-2- and -3-acetyl; 4-isoxazolyl and substituted 4-isoxazolylacetyl; pyridylacetyl, tetrazolylacetyl or a sydnoneacetyl group. The substituted 4-isoxazolyl group may be a 3-aryl-5-methyl isoxazol-4-yl group, the aryl group being e.g. phenyl or halophenyl e.g. chloro- or bromophenyl. An acyl group of this type is 3-o-chlorophenyl-5-methylisoxazol-4-yl-acetyl.

ii. $C_nH_{2n+1}$CO— where n is an integer from 1–7. The alkyl group may be straight or branched and, if desired, may be interrupted by an oxygen or sulphur atom or substituted by e.g. a cyano group, a carboxy group, an alkoxycarbonyl group, a hydroxy group or a carboxycarbonyl group (—CO.COOH). Examples of such groups include cyanoacetyl, hexanoyl, heptanoyl, octanoyl, butylthioacetyl, chloroacetyl and trichloroacetyl groups.

iii. $C_nH_{2n-1}$CO— where n is an integer from 2–7. The alkenyl group may be straight or branched and, if desired, may be interrupted by an oxygen or a sulphur atom. An example of such a group is allylthioacetyl.

iv.  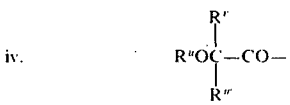

where $R^u$ has the meaning defined under (i) and in addition may be benzyl, and $R^r$ and $R^{r\prime}$ which may be the same or different each represent hydrogen, phenyl benzyl, phenethyl or lower alkyl. Examples of such groups include phenoxyacetyl, 2-phenoxy-2-phenylacetyl, 2-phenoxypropionyl, 2-phenoxybutyryl, 2-methyl-2-phenoxypropionyl, p-cresoxyacetyl and p-methylthiophenoxyacetyl.

v.  

where $R^u$ has the meaning defined under (i) and, in addition, may be benzyl and $R^r$ and $R^{r\prime}$ have the meanings defined under (iv). Examples of such groups include S-phenylthioacetyl, S-chlorophenylthioacetyl, S-fluorophenylthioacetyl, pyridylthioacetyl, and S-benzylthioacetyl.

vi. $R^u Z(CH_2)_m CO$— where $R^u$ has the meaning defined under (i) and, in addition, may be benzyl, Z is an oxygen or sulphur atom and m is an integer from 2–5. An example of such a group is S-benzylthiopropionyl.

vii. $R^u CO$— where $R^u$ has the meaning defined under (i). Examples of such groups include benzoyl, substituted benzoyl (e.g. aminobenzoyl), 4-isoxazolyl- and substituted 4-isoxazolylcarbonyl, cyclopentanecarbonyl, sydnonecarbonyl, naphthoyl and substituted naphthoyl (e.g. 2-ethoxynaphthoyl), cuinoxalinylcarbonyl and substituted quinoxalinylcarbonyl (e.g. 3-carboxy-2-quinoxalinylcarbonyl). Other possible substituents for benzoyl include alkyl, alkoxy, phenyl, phenyl substituted by carboxy, alkylamido, cycloalkylamido, allylamido, phenyl(lower)alkyl amido, morpholinocarbonyl, pyrrolidinocarbonyl, piperidinocarbonyl, tetrahydropyridino, furfurylamido or N-alkyl-N-anilino, or derivatives thereof and such substituents may be in the 2- or 2- and 6-positions. Examples of such substituted benzoyl groups are 2,6-dimethoxybenzoyl, 2-methylamidobenzoyl and 2-carboxybenzoyl. Where the group $R^u$ represents a substituted 4-isoxazolyl group, the substituents may be as set out above under (i). Examples of such 4-isoxazolyl groups are 3-phenyl-5-methyl-isoxazol-4-yl carbonyl, 3-o-chlorophenyl-5-methyl isoxazol-4-yl carbonyl and 3-(2,6-dichlorophenyl)-5-methyl-isoxazol-4-yl carbonyl.

viii.  

where $R^u$ has the meaning defined under (i) and X is amino, substituted amino (e.g. acylamido or a group obtained by reacting the α-aminoacylamido group of the 6-side chain with an aldehyde or ketone e.g. acetone, methylethylketone or ethyl acetoacetate), hydroxy, carboxy, esterified carboxy, triazolyl, tetrazolyl, cyano, halogeno, acyloxy (e.g. formyloxy or lower alkanoyloxy) or etherified hydroxy group. Examples of such acyl groups are α-aminophenylacetyl and α-carboxyphenylacetyl.

ix.  

where $R^r$, $R^y$ and $R^z$ which may be the same or different may each represent lower alkyl, phenyl or substituted phenyl. $R^x$ can also be hydrogen. An example of such an acyl group is triphenylmethylcarbonyl.

x. 

where $R^u$ has the meaning defined under (i) and in addition may be hydrogen, lower alkyl or halogen substituted lower alkyl. An example of such a group is $Cl(CH_2)_2NHCO$.

xi. 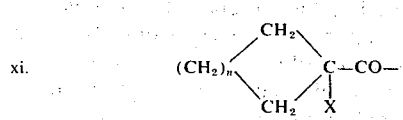

where X has the meaning defined under (viii) above and n is an integer of from 1 to 4. An example of such an acyl group is 1-aminocyclohexanecarbonyl.

xii. Amino acyl, for example $R^wCH(NH_2).(CH_2)_nCO$, where $n$ is an integer from 1–10, or $NH_2.C_nH_{2n}Ar(CH_2)_mCO$, where $m$ is zero or an integer from 1–10, and $n$ is 0,1 or 2, $R^w$ is a hydrogen atom or an alkyl, aralkyl, or carboxy group or a group as defined under $R^u$ above, and Ar is an arylene group, e.g. p-phenylene or 1,4-naphthylene. Examples of such groups are disclosed in British Patent Specification No. 1,054,806. A group of this type is the p-aminophenylacetyl group. Other acyl groups of this type include those, e.g.δ-aminoadipoyl, derived from naturally occurring amino acids and derivatives thereof e.g. N-benzoyl-δ-aminodipoyl or N-chloroacetyl-δ-aminoadipoyl.

xiii. Substituted glyoxylyl groups of the formula $R^y$.-CO.CO— where $R^y$ is an aliphatic, araliphatic or aromatic group, e.g. a thienyl group, a phenyl group, or a mono-, di- or tri- substituted phenyl group, the substituents being, for example, one or more halogen atoms (F, Cl, Br or I), methoxy groups, methyl groups or amino groups, or a fused benzene ring. Included in this group are also the α-carbonyl derivatives of the above substituted glyoxylyl groups, formed for example with hydroxylamine, semicarbazide, thiosemicarbazide, isoniazide or hydrazine.

Preferred amine protecting groups are the hydrocarbyloxycarbonyl groups (wherein the amino group forms part of a urethane), in particular alkoxycarbonyl groups such as methoxycarbonyl, ethoxycarbonyl and, most preferably t-butoxycarbonyl groups, which may carry substituents such as halogen atoms as in the 2,2,2-trichloroethoxycarbonyl group, as well as aralkoxycarbonyl groups such as benzyloxycarbonyl, p-methoxybenzyloxy-carbonyl and diphenylmethoxycarbonyl groups. Cycloalkoxycarbonyl groups are also advantageous, especially the adamantyloxycarbonyl group. The p-nitrobenzyloxycarbonyl group, which can be selectively removed by reduction e.g. hydrogenolysis, is also useful. The initial penicillins carrying protecting groups of this type may be prepared from 6-aminopenams by conventional methods for example by reaction with an appropriate haloformic ester.

It is also possible for the amino group to carry two acyl substituents which may, if desired, be derived from a dicarboxylic acid as in the phthaloyl group.

The group $R^5$ is advantageously a hydroxyl group; an esterified or etherified hydroxy group; an acylamino group e.g. a urethane group; a carboxyl group or an esterified carboxyl group.

Where $R^5$ is an etherified or esterified hydroxyl group or includes such a group as in urethanes or esterified carboxyl groups, the O- attached grouping is preferably readily cleaved to hydroxyl, for example by mild acidic, basic or enzymic hydrolysis, reduction or hydrogenolysis, to permit removal of the whole chain on the β-lactam nitrogen. Such removable groups include, in particular, the tetrahydropyranyloxy, 4-methoxy tetrahydropyranyloxy, di-(2-chloroethoxy)-methoxy, diphenylmethoxy, carbobenzoxy or trifluoroacetoxy groups. Where $R^5$ is a urethane group the terminal alcohol or phenol residue is preferably one which is readily cleaved by acidic, basic, enzymic hydrolysis, reduction or hydrogenolysis. Such alcohol residues include, in particular, 2-halo-lower alkyl groups, preferably carrying more than one halogen atom, for example a 2,2,2-trichloroethoxy or 2,2,2-trichloro-1-methylethoxy group or a 2,2,2-tribromoethoxy group; or a 2-iodoethoxy or 2-bromoethoxy group. These groups may readily be removed by reduction. The alcohol residue may also be an arylmethyl group such as a benzyl group which may be removed by hydrolysis.

Where $R^8$ is a group

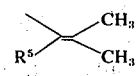

in which $R^5$ is an electron withdrawing group, particularly a carboxyl or esterified carboxyl group, the group $R^8$ can be converted into a pyrazoline derivative by reaction with a diazo reagent $N_2CHR^9$ where $R^9$ is an aliphatic, aromatic or araliphatic group, and this resulting side chain can be removed by reduction, for example with zinc and acetic acid.

Where $R^8$ is a group

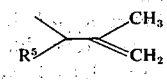

in which $R^5$ is an electron withdrawing group, this can readily be converted to the above $\Delta^2$ form by treatment with a base.

The group X in the compound of formula III may be, for example, an oxygen, nitrogen or sulphur function or a halogen atom, preferably a chlorine or bromine atom.

Suitable oxygen functions include hydroxyl, blocked hydroxyl groups such as aliphatic, aromatic and araliphatic etherified hydroxyl, esterified hydroxyl groups and stannyloxy and silyloxy groups, advantageously containing 1–20 carbon atoms. The hydrocarbon portions of these groups may thus be, for example, alkyl groups, which may contain, for example, 1–6 carbon atoms, e.g. methyl, ethyl and butyl groups, aralkyl groups, which are preferably monocyclic groups having 1–6 carbon atoms in the alkyl portion, e.g. benzyl, phenethyl and phenylpropyl groups, or monocyclic aryl groups, for example phenyl or substituted phenyl groups. Preferred oxygen functions include ethoxy, isobutyloxy and benzyloxy groups.

Suitable sulphur functions include the sulphur analogues of the oxygen functions described above, and suitable nitrogen functions include amine groups, which are preferably disubstituted and weakly basic, carrying, for example, N-aliphatic, araliphatic, cycloaliphatic or aromatic groups e.g. as defined above for the O- and S-functions.

Where the groups Y, $R^6$ and $R^7$ are other than hydrogen these may be aliphatic, araliphatic or aromatic groups advantageously containing 1–20 carbon atoms. Thus they may be for example, as more specifically defined for the hydrocarbyl groups in the O-, S- and N-functions described above.

The groups Y, $R^6$ and $R^7$ may advantageously carry a leaving function as a substituent, in order to promote cyclisation with the $\beta$-lactam nitrogen atom, or with a group attached thereto, to form a polycyclic structure such as a cepham, cephem or penam structure. Such functions include reactive ester groups such as halogen atoms, e.g. chlorine, bromine or iodine atoms and aromatic or aliphatic sulphonyloxy groups, e.g. mesyloxy or tosyloxy groups. Other possible substituents include carboxyl groups and esterified carboxyl groups, e.g. ethoxycarbonyl groups.

Cyclisation may also be promoted by introduction of a reactive group or bond into a compound of formula V or VI as a subsequent reaction.

The reaction of the penicillin 1-oxide and the compound of formula III is conveniently performed at a temperature in the range 50° – 140°C, advantageously 70°–100°C, in order to facilitate cleavage at the penicillin sulphur atom. A reaction temperature of about 80°C is preferred.

The reaction is peferably performed under neutral conditions, although small quantities of acid may in certain cases tend to accelerate the process. An insoluble acid catalyst, for example aluminium bromide or an acid ion exchange resin, may conveniently be used for this purpose. The acid is thought to aid cleavage at the penicillin sulphur atom by weakening the S—O bond of the sulphoxide grouping by protonation or complex formation.

The compound of formula III may itself act as solvent, or it may be diluted with a solvent e.g. a hydrocarbon solvent such as benzene, a halogenated hydrocarbon solvent such as carbon tetrachloride or ethylenedichloride, a cyclic ether such as dioxan or tetrahydrofuran or a nitrile solvent such as acetonitrile. The reaction should generally be performed in the substantial absence of a protic solvent.

The compounds of formulae V, VI and VII are new, and constitute a feature of the invention. The compounds are valuable intermediates in the synthesis of polycyclic structures containing a $\beta$-lactam group. As indicated above, cyclisation may be promoted by reactive substituents or bonds in the groups Y, $R^6$ or $R^7$. The carbonyl group in compounds of formula VII will in itself be capable of reaction with the $\beta$-lactam nitrogen atom, when this is unblocked, to give a modified penicillin.

A carbonyl grouping can usually be introduced into the S-bonded side chain of compounds of formula V by cleavage of the electron-donating group X. O-ethers and esters can be cleaved by such methods as acidic, basic or enzymic hydrolysis, reduction or hydrogenolysis, depending on the nature of the O-attached group. For acid hydrolysis, suitable acids include mineral acids, e.g. hydrochloric acid, and strong organic acids, e.g. trichloroacetic acid, trifluoroacetic acid or p-toluenesulphonic acid. Enol ethers containing 2-halo-lower alkoxy groups, for example 2,2,2-trichloroethoxy, 2,2,2-trichloro-1-methylethoxy, 2,2,2-tribromoethoxy, 2-iodoethoxy or 2-bromoethoxy groups may be cleaved particularly readily by reduction, e.g. with zinc and acid. Benzyl ethers may be cleaved by hydrogenolysis. If the cleavage is performed under aqueous conditions, using, for example, aqueous tetrahydrofuran or dioxan as solvent, a carbonyl group will be formed. Thus if Y is a hydrogen atom the product will be an aldehyde. Alternatively, if the hydrolysis is performed in an alcoholic medium, the product will be the corresponding acetal or ketal. Cyclic acetals and ketals may be obtained by effecting the hydrolysis in the presence of a glycol. Similarly thioacetals and thioketals may be obtained by hydrolysis in the presence of a thiol. Where X is an S-ether or ester or a corresponding N-linked group, cleavage reactions of the above type in an aqueous medium will normally yield a carbonyl group although in the case of S-derivatives, some thione may be produced. Thiones can, of course, be converted into thio acetals and ketals.

Such acetals and ketals and their S-analogues may be more readily handled in subsequent reactions than the corresponding enol ethers and esters or corresponding N- and S-derivatives from which they are produced.

In the case of acid hydrolysis, the reaction mixture is advantageously heated, preferably to a temperature in the range 40° – 100°C.

For a better understanding of the invention, the following Examples are given by way of illustration only. All temperatures are in °C. Column chromatography was carried out using Merck 0.05 – 0.2 mm silica gel. Thin-layer chromatography was carried out on Merck silica gel $F_{254}$ plates; the solvents used are given in the individual Examples. NMR spectra were obtained on a Varian HA 100 instrument, unless otherwise stated. The integrals agreed with the numbers of protons indicated. Signs were not determined for the coupling constants (J).

EXAMPLE 1

2'',2'',2''-Trichloroethyl (3''R,4''R)-2-isopropylidene-2-[3'-phenylacetamido-4'-(ethoxycarbonylmethylthioazetidin-2'-on-1'-yl]acetate A solution of (1S, 3S, 5R, 6R)-2',2',2'-trichloroethyl 6-phenylacetamidopenicillanate, 1-oxide (2.0 g, 4.15 m.mole) in ketene diethyl acetal (2 g, 29.3 m.moles) and benzene (10 mls) was refluxed for 42 hours. The mixture was evaporated to give a brown gum which was chromatographed on silica (90 g) using benzene/ethyl acetate 10:1 as solvent to give the title compound (1.57 g.68%) as a yellow gum. $\nu_{max}$ (chloroform smear): 3300 (N—H), 1770 ($\beta$-lactam), 1730 (esters), 1670 (amide), 1540 (amide) $cm^{-1}$. N.M.R. (60 MHz, $CDCl_3$, $\tau$) 2.65 (5- proton singlet, phenyl group), 2.90 (1-proton doublet, J= 8 Hz, amide proton), 4.50 (1-proton doublet, J = 5 Hz, $\beta$-lactam proton), 4.73 (proton double doublet, J = 5.8 Hz, $\beta$-lactam proton), 5.24 (2-proton A-B quartet, J = 12 Hz, —O—$CH_2CCl_3$), 5.92 (2-proton quartet, J = 7.5 Hz, —$CO_2CH_2Me$), 6.38 (2- proton singlet, benzylic protons), 6.95 (2-proton singlet, —S—$CH_2$—$CO_2Et$), 7.68 and 7.95 (3-proton singlets, geminal methyl groups), 8.74 (3-proton triplet, J = 7.5 Hz, —$CO_2CH_2CH_3$).

(Found : C, 47.8; H, 4.6; N, 5.0: $C_{22}H_{25}Cl_3N_2O_6S$ requires C, 47.9; H, 4.6; N, 5.1).

EXAMPLE 2

2''',2''',2'''-Trichloroethyl (3'R,4'R)-2-isopropylidene-2-[3'-phenylacetamido-4'-(2''-isobutyloxyvinylene-1''-yl-thioazetidin-2'-on-1'-yl]acetate A suspension of (1S,3S,5R,6R)2',2',2'-trichloroethyl 6-phenylacetamido penicillanate, 1-oxide (3.0 g, 6.23 m.mole) in vinyl isobutyl ether (50 mls) and dioxan (10 mls) was refluxed for 42 hours. The mixture was evaporated to give a brown gum which was chromatographed on silica (100 g) using benzene/ethyl acetate 10:1 as solvent to give the title compound (1.69 g 48%) as a yellow gum. $\nu_{max}$ (liquid film): 3300 (N—H), 1765 (β-lactam), 1735 (unsaturated ester), 1665 (amide), 1550 (amide)cm$^{-1}$. N.M.R. (100 M.Hz, CDCl$_3$, τ) 2.67 (5-proton singlet, phenyl group), 3.04 (1-proton doublet, J=8 Hz, amide proton), 3.54 (1-proton doublet, J=12 Hz, vinylic proton), 4.65 (1-proton double doublet, J=4.8 Hz and 8Hz, β-lactam proton), 4.86 (1-proton doublet, J=4.8 Hz, β-lactam proton), 5.12 (1-proton doublet, J=12 Hz, vinylic proton), 5.30 (2-proton A-B quartet, J=12 Hz, -CH$_2$CCl$_3$), 6.45 (2-proton singlet, benzylic protons), 6.72 (2-proton doublet J=6 Hz —O—CH$_2$.CH.Me$_2$), 7.74 and 7.98 (3-proton singlets, geminal methyl groups), 8.18 (1-proton multiplet, —OCH$_2$CHMe$_2$), 9.12 (6-proton doublet, J = 6.5 Hz, —OCH$_2$CH(CH$_3$)$_2$.

EXAMPLE 3

2''',2''',2'''-Trichloroethyl (3'R, 4'R)-2-isopropylidene-2-[3'-phenylacetamido-4'(2'',-2''-dimethoxyethan-1''-yl-thio)-azetidin-2'-on-1'-yl]acetate The crude 2''',2''',2'''-trichloroethyl (3'R, 4'R)-2-isopropylidene-2-[3'-phenylacetamido-4'-(2''-isobutyloxyvinylene-1''-yl-thi0)-azetidin-2'-on-1'-yl]acetate from Example 2 (3.5g.) was refluxed in methanol (100 mls) with 6N HCl (1 ml.) for one hour. The solvent was removed under vacuum then the product was dissolved in benzene, washed with sodium hydrogen carbonate solution, water (twice), dried over magnesium sulphate and the solvent removed to leave a dark-red gum (2.87 g). This gum was chromatographed on alumina (100 g., grade V) using benzene/ethyl-acetate 20:1 → 10:1 as eluant to give the title compound as a yellow gum. Yield 1.5 g (44%). The gum was crystallised from benzene/petrol to give colourless crystals of the title compound. m.p. 90.5° – 91.5°.[α]$_D$$^{23}$ = –15° (c, 0.90, CHCl$_3$). $\nu_{max}$ (film) 3320 (NH) 1770 (β-lactam), 1730 (unsaturated ester), 1680 (amide), 1540 cm.$^{-1}$ (amide), τ 2.74 (phenyl protons), 3.86 (NH proton, doublet, J = 8 Hz), 4.64 – 4.78 (2-protons, β-lactam protons), 5.10 and 5.45 (2-protons, AB quartet, —CH$_2$CCl$_3$), 6.40 (2-protons, singlet PhCH$_2$) 5.80 (1 proton, triplet, J = 5.5 Hz, —CH-6Me)$_2$), 6.80 (3 proton singlet, MeO), 6.83 (3 proton singlet MeO), 7.51 (2 proton doublets, J = 5.5 Hz, —SCH$_2$), 7.72 (3 proton singlet), 7.99 (3 proton singlet).

(Found : C, 47.71; H, 5.02; N, 4.98; Cl, 19.19; S, 5.80; C$_{22}$H$_{27}$N$_2$O$_6$ S Cl$_3$ requires C, 47.70; H, 4.19; N, 5.05; Cl, 19.20; S, 5.78; O, 17.13%).

EXAMPLE 4

2',2',2'-Trichloroethyl (3''R,4''R)-4,4-dimethyl-3ε-[3''-phenylacetamidoazetidin-2''-on-4''-(2''''-isobutyloxyvinylene-1''''-yl]thio-1''/-yl]-1-pyrazoline-3ε-carboxylate 2''',2''',2'''-Trichloroethyl (3'R,4'R)-2-isopropylidene-2-[3'-phenylacetamido-4'-(2''-isobutyloxyvinylene-1''-yl-thio)azetidin-2'-on-1'-yl] acetate (723 mgs, 1.28 m.mole) was dissolved in ether (25 mls) at 0°C containing a large excess of diazomethane and the mixture left to stand at 5°C for 5 days. The diazomethane was then allowed to evaporate and the solvent removed to give a mixture of the two epimers of the title compound (750 mgs 97%) as a yellow gum. N.M.R. (60 MHz, CDCl$_3$,τ): 2.68 (5-proton singlet, phenyl group), 3.08 (1-proton doublet, J= 9 Hz, amide proton), 3.34 (1-proton doublet, J=12 Hz, vinylic proton), 4.24 – 5.40 (6-proton complex - β-lactam protons, pyrazoline protons and —CH$_2$CCl$_3$), 6.32 (2-proton singlet benzylic protons), 6.60 (2-proton doublet, J = 6 Hz, —O—CH$_2$CHMe$_2$), 8.18 (1-proton multiplet, —OCH$_2$—CHMe$_2$), 8.66 and 9.02 (3-proton singlets, geminal methyl groups), 9.12 (6-proton doublet, J = 7 Hz, —O—CH$_2$CH(CH$_3$)$_2$).

EXAMPLE 5

(3R,4R)-4-(2'-Isobutyloxyvinylene-1'-yl-thio)-3-phenylacetamido-azetidin-2-one A solution of 2''',2''',2'''-trichloroethyl (3''R, 4'λ'R)-4,4-dimethyl-3ε-[3''-phenylacetamidoazetidin-2''-on-4''-(2'-isobutyloxyvinylene-1'-yl)-thio-1''-yl]-1-pyrazoline-3ε-carboxylate (4.0g., 6.4 mmole) in acetic acid (54 ml.) containing water (6 ml.) was treated with zinc dust (6g.). The reaction mixture was stirred for 1½ hr. at 22°. After filtration the filtrate was evaporated to a small volume and then partitioned between water and ethyl acetate (100 ml.). The organic phase was then washed with sodium hydrogen carbonate solution, dried and evaporated to a foam. Chromatography on silica gel (30g.) using benzene:ethyl acetate = 2:1 gave the title compound as a 2:1 mixture of cis and trans isomers (0.85 g., 38%). Trituration with ether gave a white crystalline solid m.p. 105°–110°, [α]$_D$$^{24}$ + 58° (c, 1.06, tetrahydrofuran). $\nu_{max}$ (CHBr$_3$) 3410 and 3300 (NH), 1774 (β-lactam), 1678 and 1510 cm$^{-1}$ (amide). NMR (100 MHz, CDCl$_3$, τ) 2.68 (phenyl), 3.24 (NH), 3.44 and 5.13 (trans-vinylic protons, J 12 Hz), 3.68 and 5.38 (cis-vinylic protons, J 6 Hz), 4.49 (3-H, J 4 Hz), 5.28 (4-H, J 4 Hz), 6.39 (CH$_2$Ph), 6.62 (—CH$_2$O), 8.10 (CH(CH$_3$)$_2$) and 9.09 ((CH$_3$)$_2$).

(Found: C, 60.7; H, 6.7; N, 8.5; S, 9.5; C$_{17}$H$_{22}$N$_2$O$_3$S requires C, 61.0; H, 6.6; N, 8.4; S, 9.6%).

EXAMPLE 6

2''',2''',2'''-Trichloroethyl (3''R,4''R)-2-isopropylidene-2-[3''-phenylacetamido-4''-(2'-benzyloxyvinylene-1'-yl-thio) azetidin-2''-on-1''-yl]acetate A solution of (1S,3S,5R,6R) 2',2',2'-trichloroethyl 6-phenylacetamidopenicillanate,1-oxide (3.0 g., 6.25 mmole) in dioxan (10 ml.) containing benzyl vinyl ether was heated to reflux for 6 hr. The excess solvent was removed in vacuo and the resulting oil was chromatographed on silica gel (30 g.) using benzene and benzene:ethyl acetate = 4:1 as solvent. The title compound was obtained as a gum (2.25 g., 60%), $\nu_{max}$ (bromoform) 3400 (NH), 1759 (β-lactam), 1740 (ester), 1675 and 1500 cm$^{-1}$ (NH).NMR (100 MHz, CDCl$_3$,τ) 2.68 (Phenyl), 3.4 (vinylic proton), 4.50 (3-H and 4-H), 4.89 (vinylic proton), 5.20 (—CH$_2$CCl$_3$), 5.33 (OCH$_2$Ph), 6.40 (COCH$_2$Ph), 7.98 and 8.11 (geminal methyl groups).

EXAMPLE 7

(1R,3R,4R)-4-(2'-Isobutyloxyvinylene-1'-yl-thio)-3-phenylacetamido-1-[1''-(2''',2''',2'''-trichloroethoxycarbonylamino)-2'-methylene-n-propyl-1'''-yl]azetidin-2-one A solution of (3R,5R,6R)-2,2-dimethyl-6-phenylacetamido-3-(N-2',2',2'-trichloro-ethoxycarbonylamino) penam-1R and 1S-oxides (1.0g., 2 mmole) in dioxan (5 ml.) containing isobutyl vinyl ether (25 ml.) was heated to reflux for 16 hr. Removal of the excess solvent resulted in a gum which was chromatographed on silica gel (10g.) using benzene and benzene:ethyl acetate = 3:1 as solvent to give the title compound as a foam (0.43 g., 37%).$\nu_{max}$ (bromoform) 3440 and 3350 (NH), 1760 (β-lactam), 1740 (CO$_2$R), 1675 and 1500 cm$^{-1}$ (amide). NMR (100 MHz, CDCl$_3$, τ) 2.00 (NH), 2.68 (Phenyl), 3.5 to 4.1 (olefinic protons), 4.48 (1''-H), 4.90 (vinyl protons and 3-H and 4-H), 5.18 and 5.33 (—CH$_2$CCl$_3$, AB-quartet, J 12 Hz), 6.39 (CH$_2$Ph), 6.80 (CH$_2$—CH(CH$_3$)$_2$), 8.19(—CH$_3$), 9.10 ((CH$_3$)$_2$).

The starting material for this Example may be prepared as described in Example 9 of our copending British cognate application Nos. 37189/70 and 52285/70.

A solution of 2,2-dimethyl-6β-phenylacetamido-3α-(N-2$^1$,2$^1$,2$^1$-trichloroethoxycarbonylamido)penam (1.0 g., 2.6 mole) in anhydrous tetrahydrofuran (10 ml.) was cooled to 0°. 35%-Peracetic acid (0.58 ml., 1 equiv.) was added dropwise and the reaction allowed to proceed for one-half hour. After evaporation under reduced pressure a solid was obtained, t.l.c. indicated the presence of three products, two of which were predominant (R$_f$ 0.23 and 0.13). Chromatography on Merck 0.05–0.2 mm silica gel (10 g.) with benzene:ethyl acetate = 1:1 as solvent gave the two major components (0.46 g.). One of these components, 2,2,-dimethyl-6β-phenylacetamido-3α-(N-2$^1$,2$^1$,2$^1$-trichloroethoxycarbonylamino)penam-1α-oxide, crystallised from chloroform/petroleum (b.p. 60°–80°), m.p. 159–163°, [α]$_D{}^{22}$ + 113° (c.l. tetrahydrofuran), $\nu_{max}$ (Nujol) 3330 (NH), 3240 (NH), 1780 (β-lactam), 1740 and 1240 (NHCO$_2$R), 1665 and 1525 (CONH), and 1035 cm.$^{-1}$ (SO), NMR (CDCl$_3$, τ) 1.30 (NH), 270 (Ph), 4.41 (3-H, doublet, J 9 Hz), 4.61 and 5.22 (6H and 5-H respectively, AB-quartet, J 4 Hz), 5.15 and 5.33 (AB-quartet, J 13 Hz, CH$_2$CCl$_3$), 6.40 (CH$_2$Ph), 8.57 (CH$_3$), and 8.62 (CH$_3$).

(Found: C, 43.2; H, 4.1; Cl, 21.5; N, 8.7; S, 6.5. C$_{18}$H$_{20}$Cl$_3$N$_3$O$_5$S requires C, 43.5; H, 4.0; Cl, 21.5; N, 8.5; S, 6.5%).

The mother-liquor from the above crystallisation was found to contain the non-crystalline 2,2-dimethyl-6β-phenylacetamido-3α-(N-2$^1$,2$^1$,2$^1$-trichloroethoxycarbonylamino)penam-1α-oxide, $\nu_{max}$ (Nujol) 3300 (NH), 1800 (β-lactam), 1736 and 1518 (NHCO$_2$R), 1670 and 1530 cm$^{-1}$(CONH), NMR (CDCl$_3$, τ) 2.70 (Ph), 4.1 (6-H, 5-H and NH, multiplet), 6.45 (CH$_2$Ph), 8.46 (CH$_3$), and 8.79 (CH$_3$).

EXAMPLE 8

2'',2'',2''-Trichloroethyl (3'R,4'R)-4,4-Dimethyl-3ε-[4'-ethoxycarbonylmethylthio-3'-phenylacetamidoazetidin-2'-on-1'-yl]-1-pyrazoline-3ε-carboxylate A solution of 2'',2'',2''-trichloroethyl (3'R,4'R)-2-isopropylidene-2-(3'-phenylacetamido-4'-ethoxycarbonylmethylthio-azetidin-2'-on-1'-yl)acetate (0.685g, 1.1 mmole) in ether (60 ml.) containing diazomethane prepared from n-nitrosomethyl urea (3g, 0.03 mole) was allowed to stand at 0° for 7 days. The excess diazomethane was removed by evaporation and the crude product passed down a celite column. Removal of the solvent gave a gum (0.724g., 98%). $\nu_{max}$ (chloroform smear) 3300 (NH), 1770 (β-lactam), 1750 (ester) and 1680 cm$^{-1}$ (amide): NMR (100 MHz, CDCl$_3$, τ) 2.7 (Phenyl), 3.4 (NH), 4.35 (3-H and 4-H), 5.20 (—CH$_2$CCl$_3$), 5.80 (—OCH$_2$CH$_3$), 6.25 (CH$_2$Ph), 6.55 (—SCH$_2$), 7.70 (—CH$_2$N—), 8.6 ((CH$_3$)$_2$) and 9.0 (—CH$_2$CH$_3$).

EXAMPLE 9

Ethyl (3'R,4'R)-(3'-Phenylacetamidoazetidin-2'-on-1'-yl)-thio-2-acetate

A solution of 2'',2'',2''-trichloroethyl (3'R,4'R)-4,4-dimethyl-3ε-[4'-ethoxycarbonylmethylthio-3'-phenylacetamido-azetidin-2'-on-1'-yl]-1-pyrazoline-3ε-carboxylate (0.73 g., 1.2 mmole) in 10% aqueous acetic acid (60 ml.) was stirred with zinc powder (1.5 g.) for 4 hr. at 20°. After filtration the filtrate was evaporated in vacuo to give an oil which was extracted with ethyl acetate; washing with water, sodium hydrogen carbonate solution, drying and evaporation gave a yellow crystalline solid (300 mg.). This product was chromatographed on silica gel (6g.) using benzene:ethyl acetate = 10:1 and 2:1 as solvent. The title compound was obtained as yellow solid (195 mg. 50%) which crystallised from ethyl acetate/petrol (b.p. 60° to 80°) solvent mixture, m.p. 118.5° to 120°. [α]$_D{}^{22}$ + 17° (c, 0.97, chloroform).$\nu_{max}$ (chloroform) 3300 (NH), 1770 (β-lactam), 1730 (ester) and 1680 cm$^{-1}$ (amide). MNR (100 MHz, CDCl$_3$, τ) 2.65 (Phenyl), 3.1 (NH), 4.50 and 4.90 (3-H and 4-H respectively, J 4 Hz), 5.80 (—OCH$_2$CH$_3$), 6.35 (—CH$_2$Ph), 6.80 (—CH$_2$S) and 8.70 (—CH$_2$CH$_3$). (Found: C, 55.9; H, 5.8; N, 8.8; S, 9.8:C$_{15}$H$_{18}$N$_2$O$_4$S requires C, 55.9; H, 5.6; N, 8.7; S, 9.9%).

We claim:

1. A process for the production of azetidin-2-ones having the formula:

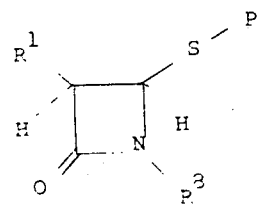

wherein P is a saturated or unsaturated, substituted or unsubstituted aliphatic group having at least 2 carbon atoms. R$^1$ is an amino or blocked amino group, and R$^x$ represents a hydrogen atom or a group of the formula

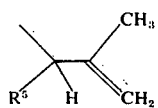

or

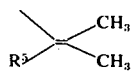

where $R^5$ represents a hydrogen atom, a protected hydroxyl or amino group, a carboxyl or blocked carboxyl group or a $C_{1-20}$ alkyl group; which comprises cleaving at a temperature of 50°–140°C a compound of the formula

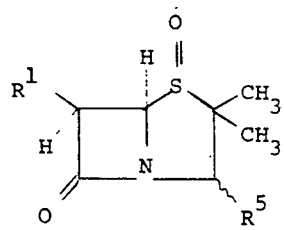

(II)

wherein $R^1$ is as defined and $R^5$ represents a hydrogen atom, a hydroxyl or amino group, a protected hydroxy or amino group, a carboxyl or blocked carboxyl group or an alkyl group having 1–20 carbon atoms, in the presence of the compound of the formula:

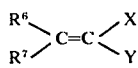

(III)

wherein X and Y, which may be the same or different, each represents a hydrogen atom, a halogen atom, or a blocked OH or SH group; and $R^6$ and $R^7$ which may be the same or different, each represents a hydrogen atom, $C_{1-20}$ alkyl, monocyclic aryl alkyl having 1–6 carbon atoms in the alkyl portion or such groups which may be substituted by mesyloxy, tosyloxy, or ethoxycarbonyl groups or halogen, or $R^7$ and Y together constitute a carbon-carbon bond.

2. A process as claimed in claim 1 wherein a compound of formula II as defined in claim 1 is reacted with a compound of formula III wherein $R^6$ represents a hydrogen atom and $R^7$, X and Y are as defined in claim 1 whereby there is obtained a compound of formula

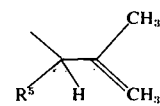

V wherein $R^1$, $R^7$, X and Y are as defined in claim 1; and $R^8$ represents a hydrogen atom or a group of formula

or

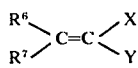

where $R^5$ is as defined in claim 1 other than a free amino or hydroxyl group.

3. A process as claimed in claim 1 wherein a compound of formula II as defined in claim 1 is reacted with a compound of formula III as defined in claim 1 with the proviso that $R^7$ and Y do not together constitute a carbon-carbon bond whereby there is obtained a compound of formula

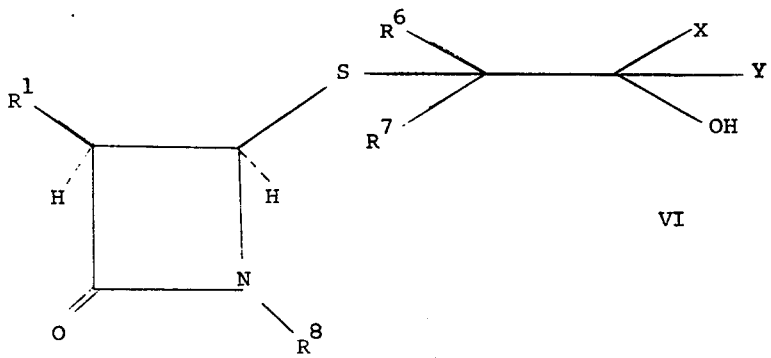

VI where $R^1$, $R^6$, $R^7$ and X are as defined in claim 1 and $R^8$ is as defined in claim 2.

4. A process as claimed in claim 1 wherein the cleavage reaction is effected at a temperature of about 80°C.

5. A process as claimed in claim 1 wherein the cleavage reaction is effected under neutral conditions.

6. A compound of the formula V

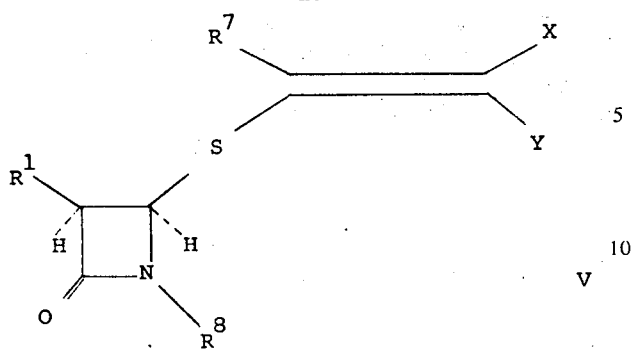

wherein $R^1$ represents an amino group or a blocked amino group; X and Y which may be the same or different, each represents a hydrogen atom, a halogen atom, or a blocked OH or SH group; and $R^7$ represents a hydrogen atom, $C_{1-20}$ alkyl, monocyclic aryl alkyl having 1–6 carbon atoms in the alkyl portion or such groups which may be substituted by mesyloxy, tosyloxy or ethoxycarbonyl groups or halogen; and $R^8$ represents a hydrogen atom or a group of the formula

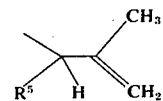

or

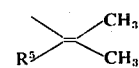

where $R^5$ represents a hydrogen atom, a protected hydroxyl or amino group, a carboxyl or blocked carboxyl group or a $C_{1-20}$ alkyl group.

* * * * *